US012146052B2

(12) United States Patent
Zia et al.

(10) Patent No.: US 12,146,052 B2
(45) Date of Patent: Nov. 19, 2024

(54) POLYMER COMPOSITION WITH MOLD RELEASE PROPERTIES

(71) Applicant: Celanese International Corporation, Irving, TX (US)

(72) Inventors: Qamer Zia, Raunheim (DE); Kirsten Markgraf, Weinheim (DE); Dirk Zierer, Hattersheim (DE); Patrick Nickolay, Villmar (DE)

(73) Assignee: CELANESE INTERNATIONAL CORPORATION, Irving, TX (US)

( * ) Notice: Subject to any disclaimer, the term of this patent is extended or adjusted under 35 U.S.C. 154(b) by 0 days.

(21) Appl. No.: 17/724,982

(22) Filed: Apr. 20, 2022

(65) Prior Publication Data
US 2022/0332941 A1    Oct. 20, 2022

Related U.S. Application Data

(60) Provisional application No. 63/319,531, filed on Mar. 14, 2022, provisional application No. 63/208,250,
(Continued)

(51) Int. Cl.
*C08L 67/02* (2006.01)
*A61M 5/31* (2006.01)
(Continued)

(52) U.S. Cl.
CPC ............... *C08L 67/02* (2013.01); *A61M 5/31* (2013.01); *C08K 3/34* (2013.01); *C08K 7/14* (2013.01);
(Continued)

(58) Field of Classification Search
CPC .......... C08L 67/02; C08L 23/06; C08L 83/04; C08L 23/0869; C08K 7/14; C08K 3/34
See application file for complete search history.

(56) References Cited

U.S. PATENT DOCUMENTS 3,822,227 A * 7/1974 Hermann ................ C08L 23/02
524/521
6,046,141 A * 4/2000 Kurz ....................... C08L 77/02
524/487
(Continued)

FOREIGN PATENT DOCUMENTS

CN    1537891 A    10/2004
CN    101910304 A    12/2010
(Continued)

OTHER PUBLICATIONS

Licowax (r) E powder; Ester of montanic acids with multifunctional alcohols (attached) (Year: 2015).*
(Continued)

*Primary Examiner* — Marc S Zimmer
*Assistant Examiner* — Surbhi M Du
(74) *Attorney, Agent, or Firm* — DORITY & MANNING, P.A.

(57) ABSTRACT

A fiber reinforced thermoplastic polymer composition is disclosed that contains at least one mold release agent. The mold release agent can comprise a polar material and/or a non-polar material. In one embodiment, both a polar wax and a non-polar wax are used. The polymer composition may also contain one or more tribological modifiers. The tribological modifier may comprise an ultra-high molecular weight silicone.

24 Claims, 2 Drawing Sheets

Related U.S. Application Data filed on Jun. 8, 2021, provisional application No. 63/177,210, filed on Apr. 20, 2021.

(51) Int. Cl.
*C08K 3/34* (2006.01)
*C08K 7/14* (2006.01)
*C08L 23/06* (2006.01)
*C08L 23/08* (2006.01)
*C08L 83/04* (2006.01)
*C08L 91/06* (2006.01)

(52) U.S. Cl.
CPC ........... *C08L 23/06* (2013.01); *C08L 23/0869* (2013.01); *C08L 83/04* (2013.01); *C08L 91/06* (2013.01); *C08L 2205/025* (2013.01); *C08L 2205/035* (2013.01)

(56) References Cited

U.S. PATENT DOCUMENTS

| | | |
|---|---|---|
| 6,447,913 B1 | 9/2002 | Watanabe et al. |
| 6,512,027 B2 | 1/2003 | Kanai et al. |
| 6,569,931 B2 | 5/2003 | Furukawa et al. |
| 7,652,079 B2 | 1/2010 | Takayama et al. |
| 7,855,238 B2 | 12/2010 | Cohoon et al. |
| 7,923,504 B2 | 4/2011 | Schachtely et al. |
| 7,923,506 B2 | 4/2011 | Cohoon et al. |
| 8,070,710 B2 | 12/2011 | Dougherty, Jr. |
| 8,084,538 B2 | 12/2011 | Mawatari et al. |
| 8,106,132 B2 | 1/2012 | Tan et al. |
| 8,415,430 B2 | 4/2013 | Kuhn et al. |
| 8,546,469 B2 | 10/2013 | Lee et al. |
| 8,734,956 B2 | 5/2014 | Sakata et al. |
| 9,062,165 B2 | 6/2015 | Meller et al. |
| 9,150,724 B2 | 10/2015 | Willem et al. |
| 9,290,719 B2* | 3/2016 | Mujkic ............. C11C 1/02 |
| 9,499,682 B2 | 11/2016 | Yamada |
| 9,884,953 B2 | 2/2018 | Sakata |
| 9,957,388 B2 | 5/2018 | Yamanaka et al. |
| 2003/0233070 A1 | 12/2003 | De La Serna et al. |
| 2010/0168317 A1 | 7/2010 | Cahoon-Brister |
| 2010/0309571 A1 | 12/2010 | Watari et al. |
| 2012/0246873 A1 | 10/2012 | Konduri et al. |
| 2016/0257805 A1 | 9/2016 | Markgraf et al. |
| 2017/0190906 A1* | 7/2017 | Mutou ............. G02B 5/0808 |
| 2018/0258241 A1 | 9/2018 | Zia et al. |
| 2019/0184681 A1 | 6/2019 | Iyo et al. |

FOREIGN PATENT DOCUMENTS

| | | |
|---|---|---|
| CN | 102516789 A | 6/2012 |
| CN | 103525041 A | 1/2014 |
| CN | 104845297 A | 8/2015 |
| CN | 109553935 | 4/2019 |
| JP | 2007092038 A | 4/2007 |
| KR | 20040060386 A | 7/2004 |

OTHER PUBLICATIONS

International Search Report Corresponding to Application No. PCT/US2022/025509 on Jun. 10, 2022.

\* cited by examiner

POLYMER COMPOSITION WITH MOLD RELEASE PROPERTIES

RELATED APPLICATIONS

The present application is based upon and claims priority to U.S. Provisional Patent Application Ser. No. 63/177,210, having a filing date of Apr. 20, 2021; U.S. Provisional Patent Application Ser. No. 63/208,250, having a filing date of Jun. 8, 2021; and U.S. Provisional Patent Application Ser. No. 63/319,531, having a filing date of Mar. 14, 2022, which are all incorporated herein by reference.

BACKGROUND

Engineering thermoplastics and elastomeric materials are often used in numerous and diverse applications in order to produce molded parts and products. For instance, thermoplastic polymers are used to produce all different types of molded products, such as injection molded products, blow molded products, and the like. Thermoplastic polymers, for instance, can be formulated in order to be chemically resistant, to have excellent strength properties and, when formulating compositions containing elastomers, to be flexible. Of particular advantage, many polymers can be melt processed due to their thermoplastic nature. In addition, many polymers can be recycled and reprocessed.

One objective in producing molded parts from thermoplastic polymers is the ability to quickly mold the parts and increase productivity. Each polymer formulation, for instance, can present a unique set of problems related to the melt processing characteristics of the composition which can create longer cycle times, cause mold deposits to form, and/or negatively impact the ability to remove the part from a mold. Consequently, ideally a thermoplastic composition is formulated so as to form a stable melt at the melt processing conditions. In many applications, faster crystallization rates and/or faster melt-solidification rates are desirable in order to shorten cycle times.

In view of the above, the present disclosure is particularly directed to polymer compositions that have improved melt processing characteristics. Alternatively, the present disclosure is also directed to formulating polymer compositions so as to reduce mold deposits and/or reduce the force needed in order to eject parts and articles from molds. In one embodiment, the present disclosure is directed to a formulated polymer composition that is improved in at least one of the above characteristics and can be formulated to be completely safe for food contact applications.

SUMMARY

The present disclosure is generally directed to a thermoplastic polymer composition containing a mold release package. The mold release package can reduce mold deposits and/or reduce the amount of force needed in order to remove a part or article from a mold after a molding process, such as an injection molding process. It was also unexpectedly discovered that the mold release package of the present disclosure can also influence in a positive way the melt processing characteristics and behavior of various different polymer compositions. Consequently, in one aspect, the mold release package of the present disclosure can be used to reduce molding cycle times when formulated with various polymers.

In one aspect, all of the components contained in the polymer composition are approved for use for medical applications and/or food contact applications. For instance, each polymer component contained in the polymer composition can be approved for use according to the United States Food and Drug Administration standards as codified in 21 CFR 177. For example, the components of the mold release package can be selected such that the components meet all governmental regulations regarding use in food handling applications and/or medical applications.

The polymer composition contains a thermoplastic matrix polymer. The thermoplastic polymer can comprise, for instance, a polyamide polymer, a polyester polymer, a polyether ether ketone polymer, a polyphenylene sulfide polymer, or a polyacetal polymer. For example, the thermoplastic polymer can be a polybutylene terephthalate polymer or a polyoxymethylene polymer. The thermoplastic matrix polymer can be present in the polymer composition generally in an amount greater than about 40% by weight, such as in an amount greater than about 50% by weight, such as in an amount greater than about 60% by weight, such as in an amount greater than about 65% by weight. The thermoplastic matrix polymer is generally present in the polymer composition in an amount less than about 99% by weight, such as in an amount less than about 90% by weight, such as in an amount less than about 80% by weight.

The polymer composition generally contains at least one of a nucleant, a tribological modifier, or reinforcing fibers. When containing reinforcing fibers, the reinforcing fibers, for instance, can be glass fibers. Incorporating reinforcing fibers into the polymer composition can create problems during the molding process. Fiber reinforced compositions, for instance, have a tendency to create mold deposits and may also increase the ejection forces necessary in order to remove a part from a mold. When the composition contains reinforcing fibers, however, one or more mold release agents can be present in the composition that counteract the above negative effects. When contained in the composition, the reinforcing fibers can be present in the composition generally in an amount greater than about 5% by weight, such as in an amount greater than about 10% by weight, such as in an amount greater than about 15% by weight. The reinforcing fibers are generally present in an amount less than about 50% by weight, such as in an amount less than about 45% by weight, such as in an amount less than about 35% by weight.

As described above, the polymer composition further contains at least one mold release agent. In one aspect, for instance, the polymer composition can contain a single mold release agent comprising a polar polymer. Alternatively, the polymer composition can contain a first mold release agent and a second mold release agent. The first mold release agent can be a polar polymer, while the second mold release agent can be a non-polar polymer. The first mold release agent and the second mold release agent can be present in the polymer composition at a weight ratio of from about 10:1 to about 1:10, such as from about 5:1 to about 1:5, such as from about 2:1 to about 1:2, such as from about 1.8:1 to about 1:1.8.

In one embodiment, all of the mold release agents present in the polymer composition can be approved for food handling and/or medical applications. The polar polymer that comprises the first mold release agent, for instance, can be a polyolefin polymer, such as a polyethylene polymer. In one embodiment, for instance, the polar polymer can be an oxidized polyethylene wax.

The non-polar polymer that comprises the second mold release agent, on the other hand, can also be a polyolefin polymer. For instance, the non-polar polymer can be a polyethylene wax.

In one aspect, the polymer composition can be formulated so as to contain only a single mold release agent, such as a polar mold release agent. The polar mold release agent, for instance, can have an acid value of generally greater than about 5 KOH/g, such as greater than about 10 KOH/g, such as greater than about 15 KOH/g, and generally less than about 90 KOH/g, such as less than about 70 KOH/g, such as less than about 60 KOH/g. The acid value of the polar mold release agent, for instance, can be selected based upon the particular application and the components contained in the polymer composition. In one embodiment, for instance, the acid value of the polar mold release agent can be from about 13 KOH/g to about 23 KOH/g, such as from about 15 KOH/g to about 19 KOH/g. Alternatively, the polar mold release agent can have a higher acid value. For example, in an alternative embodiment, the polar mold release agent can have an acid value of from about 40 KOH/g to about 60 KOH/g, such as from about 45 KOH/g to about 55 KOH/g.

The polar mold release agent can comprise an oxidized wax. For example, the polar mold release agent can be an oxidized polyethylene wax. Alternatively, the polar mold release agent can be oxidized esters of fatty acids. The oxidized esters of fatty acids, for instance, can be derived from biomass, such as rice bran. In one aspect, the oxidized esters of fatty acids can be derived from a blend of different fatty acids with different carbon chain lengths. In one aspect, for instance, the oxidized esters of fatty acids can be derived from greater than 50% by weight of fatty acids having a carbon chain length of from about 20 carbon atoms to about 40 carbon atoms. The oxidized esters of fatty acids can also be derived from a blend of fatty acids in which 25% by weight of the fatty acids or greater are derived from fatty acids having a carbon chain length of from about 40 carbon atoms to about 64 carbon atoms.

Each mold release agent contained in the polymer composition can generally be present in the composition in an amount less than about 2% by weight, such as in an amount less than about 1% by weight, such as in an amount less than about 0.8% by weight, such as in an amount less than about 0.5% by weight, such as in an amount less than about 0.4% by weight. Each mold release agent is generally present in the polymer composition in an amount greater than about 0.01% by weight, such as in an amount greater than about 0.08% by weight.

The one or more mold release agents serve to minimize mold deposits and can also reduce the force needed to remove a molded part from the mold. For instance, when tested according to the part ejection test, the polymer composition of the present disclosure can display an ejection force of less than about 700 N.

In one embodiment, the polymer composition can optionally contain one or more tribological modifiers. The tribological modifier, in one embodiment, can comprise an ultra-high molecular weight silicone. The ultra-high molecular weight silicone can have a kinematic viscosity of greater than about 100,000 mm$^2$ s$^{-1}$. For example, the ultra-high molecular weight silicone can be present in the polymer composition in an amount from about 0.1% to about 10% by weight, such as from about 0.5% to about 3% by weight. In one embodiment, the ultra-high molecular weight silicone comprises a polydimethylsiloxane.

In an alternative embodiment, the tribological modifier contained within the polymer composition may comprise a polytetrafluoroethylene polymer. The polytetrafluoroethylene polymer may be present alone or in combination with an ultra-high molecular weight silicone.

The polymer composition can be formulated to have low friction properties. For instance, the polymer composition can exhibit a dynamic coefficient of friction according to VDA 230-206 of less than about 0.08 when tested against a polycarbonate/ABS blend (CYCOLOY 01204H from Sabic) at a speed of 8 mm/s, at a load of 30 N and after 1,000 cycles. In one embodiment, the polymer composition may exhibit a dynamic coefficient of friction of less than about 0.07, such as less than about 0.05 when tested against the above material.

When an ultra-high molecular weight silicone is present in the composition, the silicone can be added with a carrier. In one embodiment, for instance, the ultra-high molecular weight silicone can be grafted to silica and added to the composition. Alternatively, the ultra-high molecular weight silicone may be combined with a carrier polymer prior to being blended with the other components. The carrier polymer, for instance, may comprise a polycarbonate polymer or a polyester polymer. The polyester polymer, for instance, may comprise polyethylene terephthalate, a copolyester, and/or a polyester elastomer.

The polymer composition of the present disclosure can also contain a nucleant. In one aspect, the nucleant can be a mineral nucleant. The mineral nucleant can comprise talc and can be present in the polymer composition in an amount from about 0.01% by weight to about 1% by weight.

In one embodiment, the polymer composition of the present disclosure is formulated for producing medical products. When producing medical products, for instance, the polymer composition can be formulated to be isocyanate-free.

In one embodiment, the polymer composition can be used to produce medical inhalers, injection devices, surgical instruments, wearable devices, and the like. The medical product, for instance, may include a first sliding member in operative association with a second sliding member. The first sliding member and the second sliding member may be positioned to remain in contact and move relative to each other. At least one of the sliding members can be made from the polymer composition of the present disclosure. In one embodiment, for instance, both sliding members are made from the polymer composition of the present disclosure.

Other features and aspects of the present disclosure are discussed in greater detail below.

BRIEF DESCRIPTION OF THE DRAWINGS

A full and enabling disclosure of the present disclosure is set forth more particularly in the remainder of the specification, including reference to the accompanying figures, in which.

Figure 1:
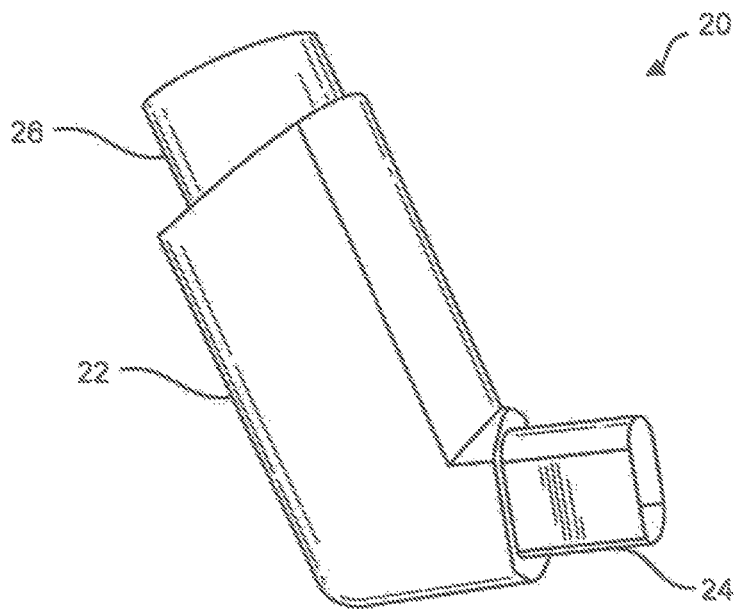
FIG. 1 is a perspective view of a medical inhaler made in accordance with the present disclosure.

Repeat use of reference characters in the present specification and drawings is intended to represent the same or analogous features or elements of the present invention.

DETAILED DESCRIPTION

It is to be understood by one of ordinary skill in the art that the present discussion is a description of exemplary embodiments only and is not intended as limiting the broader aspects of the present disclosure.

In general, the present disclosure is directed to a thermoplastic polymer composition and to polymer articles made from the composition that not only have excellent strength properties but also have improved mold release properties. Polymer compositions formulated in accordance with the present disclosure, for instance, can exhibit reduced mold deposits and/or can lower ejection forces necessary for part removal from the molds. In one embodiment, the mold release package of the present disclosure can also be used to dramatically improve the melt processing behavior of the polymer composition. For instance, it is believed that the mold release package can facilitate formation of a stable melt at the melt processing conditions and can increase crystallization rates and/or melt-solidification rates. In this manner, shorter cycle times can be observed leading to increased productivity.

The mold release package of the present disclosure contains at least one mold release agent optionally in combination with a nucleant, such as a mineral nucleant. The at least one mold release agent can be a polar mold release agent, such as an oxidized wax.

In one embodiment, the polymer composition contains a mold release package including a first mold release agent and a second mold release agent. In one embodiment, the first mold release agent is a polar polymer while the second mold release agent is a non-polar polymer. The combination of the first mold release agent and the second mold release agent can exhibit a synergistic effect that reduces mold deposits in an injection molding process and/or can lower ejection forces. Lowering mold deposits minimizes the necessity for tool cleaning and low ejection forces allows for easy part removal.

In the past, lubricants were added to polymer compositions for reducing mold deposits. For example, one particular type of lubricant used in the past were esters of montanic acid. Esters of montanic acid, however, are not approved for use in food handling and/or medical applications according to many governmental agencies. Consequently, one aspect of the present disclosure is directed to incorporating one or more mold release agents into the polymer composition that are not only approved for food handling or medical applications but also perform similarly to lubricants used in the past.

In this regard, the polymer composition of the present disclosure can be formulated so that every component contained in the composition meets governmental regulations regarding food handling or medical applications. For example, every component contained in the polymer composition can be approved for use according to the United States Food and Drug Administration food contact standards and approved listings as found in Title 21 of the Code of Federal Regulations (as in existence in March of 2021). For example, each polymer contained within the polymer composition can be approved for food handling applications as indicated in 21 CFR 177. Each component contained in the polymer composition can also be approved for food handling applications according to 21 CFR 174.

Each component contained within the polymer composition can also meet or exceed all food contact standards such as Regulation (EC) No. 1935/2004, 2023/2006, 10/2011, Resolution AP (89) 1, Germany BfR IX, Spain Real Decreto 847/2011, and Italy Decreto 21/3/73; and Chinese food contact standards such as GB 9685-2016.

In addition to a thermoplastic polymer and one or more mold release agents, the polymer composition of the present disclosure can also optionally contain one or more tribological modifiers, reinforcing fibers and/or a nucleant.

The composition of the present disclosure can be formulated for medical applications that require low friction properties. For example, when used in medical applications, the polymer composition can contain no isocyanates, epoxy resins, carbodiimides or other similar compounds. In certain applications, medical devices are needed in which the parts are not only made from high strength materials but that can provide ultra-low friction and reduced wear for parts that are intended to slide against an adjacent surface. As will be described in greater detail below, polymer compositions made according to the present disclosure have not only excellent strength properties but can display extremely low friction properties.

When two opposing surfaces slide against each other, the surfaces react in a way that is referred to as the stick-slip phenomenon. The stick-slip phenomenon refers to the manner in which two opposing surfaces or articles slide over each other in reaction to the forces of friction. Static friction refers to the friction between two or more objects that are not moving relative to each other. Kinetic friction, on the other hand, occurs when two objects are moving relative to each other while remaining in contact. In order for one object to slide relative to another object, enough force must be exerted on one object to overcome the forces of static friction. When movement between the two objects occurs, a reduction of the friction between the two surfaces can cause a sudden increase in the velocity of movement. In other words, once one object moves relative to another object, in some applications, less force is needed to continue movement. The friction between the two surfaces can increase or decrease during movement depending upon numerous factors, including the speed at which movement continues. Stick-slip describes how surfaces alternate between sticking to each other and sliding over each other as movement occurs between two surfaces and as the conditions of movement change.

Polymer articles that have a relatively high coefficient of friction not only require greater amounts of force in order to slide one material over the other but also can be prone to wear. Over time, for instance, the materials can begin to degrade due to the forces of friction.

In one aspect, the polymer composition of the present disclosure can optionally contain one or more tribological modifiers for producing molded articles having low friction characteristics. The molded articles are particularly well suited for use in medical and/or food handling applications. For example, in one embodiment, the present disclosure is directed to a low friction assembly that includes a first sliding member in operative association with a second sliding member. The first sliding member and the second sliding member can both be made from a polymer composition formulated in accordance with the present disclosure. When tested against each other or against a polycarbonate/ABS blend (CYCOLOY 01204H from Sabic), the composition can be formulated so as to exhibit a dynamic coefficient of friction of less than about 0.08, such as less than about 0.07, such as less than about 0.06, such as less than about 0.05. The compositions or molded parts can be tested against each other according to a stick-slip test having Test No. VDA 230-206.

Specimens tested using the above method can also be analyzed to measure a wear track width which is an abrasion width. In accordance with the present disclosure, the compositions and molded articles can exhibit a wear track width of less than 0.3 mm, such as less than about 0.25 mm, such as even less than about 0.2 mm when tested at a force of 30 N and at a velocity of 8 mm/s after 1,000 cycles.

The thermoplastic polymer used as the matrix polymer to form molded articles in accordance with the present disclosure can vary depending upon the particular application and the desired result. Thermoplastic polymers that may be used in accordance with the present disclosure include, for instance, a polyamide polymer, a polyester polymer, a polyether ether ketone polymer, a polyphenylene sulfide polymer, or a polyacetal polymer, and combinations thereof.

In particular embodiments, the thermoplastic polymer can be a polybutylene terephthalate polymer alone or in combination with a polyethylene terephthalate polymer. Alternatively, the thermoplastic polymer can be a polyoxymethylene copolymer.

Polyester Polymer

In one embodiment, the thermoplastic matrix polymer contained in the polymer composition comprises one or more polyester polymers. The polyester polymer generally comprises a polyalkylene terephthalate polymer.

Polyalkylene terephthalate polymers suitable for use herein are derived from an aliphatic or cycloaliphatic diol, or mixtures thereof, containing from 2 to about 10 carbon atoms and an aromatic dicarboxylic acid.

The polyesters which are derived from a cycloaliphatic diol and an aromatic dicarboxylic acid are prepared by condensing either the cis- or trans-isomer (or mixtures thereof) of, for example, 1,4-cyclohexanedimethanol with the aromatic dicarboxylic acid.

Examples of aromatic dicarboxylic acids include isophthalic or terephthalic acid, 1,2-di(p-carboxyphenyl)ethane, 4,4'-dicarboxydiphenyl ether, etc., and mixtures of these. All of these acids contain at least one aromatic nucleus. Fused rings can also be present such as in 1,4- or 1,5- or 2,6-naphthalene-dicarboxylic acids. In one embodiment, the dicarboxylic acid is terephthalic acid or mixtures of terephthalic and isophthalic acid.

In one embodiment, the polyalkylene terephthalate polymer present in the polymer composition comprises a polybutylene terephthalate polymer. For example, the polymer composition may contain a polybutylene terephthalate polymer in an amount greater than about 30% by weight, such as in an amount greater than about 40% by weight, such as in an amount greater than about 50% by weight, such as in an amount greater than about 60% by weight, such as in an amount greater than about 70% by weight. The polybutylene terephthalate polymer is generally present in an amount less than about 90% by weight, such as in an amount less than about 80% by weight.

The polymer composition may contain the polybutylene terephthalate polymer alone or in combination with other thermoplastic polymers. For instance, the polybutylene terephthalate polymer may be combined with other polyester polymers and/or a polycarbonate polymer. Other polyester polymers that may be present in the composition include a polyethylene terephthalate polymer or a polyethylene terephthalate copolymer. For instance, a polyethylene terephthalate copolymer or modified polyethylene terephthalate polymer can be produced with a modifying acid or a modifying diol.

As used herein, the terms "modifying acid" and "modifying diol" are meant to define compounds, which can form part of the acid and diol repeat units of a polyester, respectively, and which can modify a polyester to reduce its crystallinity or render the polyester amorphous. In one embodiment, however, the polyesters present in the polymer composition of the present disclosure are non-modified and do not contain a modifying acid or a modifying diol.

Examples of modifying acid components may include, but are not limited to, isophthalic acid, phthalic acid, 1,3-cyclohexanedicarboxylic acid, 1,4-cyclohexane dicarboxylic acid, 2,6-naphthaline dicarboxylic acid, succinic acid, glutaric acid, adipic acid, sebacic acid, suberic acid, 1,12-dodecanedioic acid, and the like. In practice, it is often preferable to use a functional acid derivative thereof such as the dimethyl, diethyl, or dipropyl ester of the dicarboxylic acid. The anhydrides or acid halides of these acids also may be employed where practical. Preferred is isophthalic acid.

Examples of modifying diol components may include, but are not limited to, neopentyl glycol, 1,4-cyclohexanedimethanol, 1,2-propanediol, 1,3-propanediol, 2-Methy-1,3-propanediol, 1,4-butanediol, 1,6-hexanediol, 1,2-cyclohexanediol, 1,4-cyclohexanediol, 1,2-cyclohexanedimethanol, 1,3-cyclohexanedimethanol, 2,2,4,4-tetramethyl 1,3-cyclobutane diol, Z,8-bis(hydroxymethyltricyclo-[5.2.1.0]-decane wherein Z represents 3, 4, or 5; 1,4-Bis(2-hydroxyethoxy)benzene, 4,4'-Bis(2-hydroxyethoxy) diphenylether [Bis-hydroxyethyl Bisphenol A], 4,4'-Bis(2-hydroxyethoxy)diphenylsulfide [Bis-hydroxyethyl Bisphenol S] and diols containing one or more oxygen atoms in the chain, e.g. diethylene glycol, triethylene glycol, dipropylene glycol, tripropylene glycol, and the like. In general, these diols contain 2 to 18, preferably 2 to 8 carbon atoms. Cycloalphatic diols can be employed in their cis or trans configuration or as mixtures of both forms.

When present, the polyester polymer combined with the polybutylene terephthalate can be added to the polymer composition in amounts generally greater than about 5% by weight, such as in amounts greater than about 10% by weight, such as in amounts greater than about 12% by weight. The polyester polymer is generally present in an amount less than about 40% by weight, such as in an amount less than about 30% by weight, such as in an amount less than about 20% by weight, such as in an amount less than about 15% by weight.

Polyoxymethylene Polymer

In one embodiment, the thermoplastic matrix polymer can be a polyoxymethylene polymer, such as a polyoxymethylene homopolymer or a polyoxymethylene copolymer. According to one embodiment, the polyoxymethylene is a homo- or copolymer which comprises at least 50 mol. %, such as at least 75 mol. %, such as at least 90 mol. % and such as even at least 97 mol. % of —CH$_2$O— repeat units.

In one embodiment, a polyoxymethylene copolymer is used. The copolymer can contain from about 0.01 mol. % to about 20 mol. % and in particular from about 0.5 mol. % to about 10 mol. % of repeat units that comprise a saturated or ethylenically unsaturated alkylene group having at least 2 carbon atoms, or a cycloalkylene group, which has sulfur atoms or oxygen atoms in the chain and may include one or more substituents selected from the group consisting of alkyl cycloalkyl, aryl, aralkyl, heteroaryl, halogen or alkoxy. In one embodiment, a cyclic ether or acetal is used that can be introduced into the copolymer via a ring-opening reaction.

Preferred cyclic ethers or acetals are those of the formula:

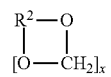

in which x is 0 or 1 and $R^2$ is a $C_2$-$C_4$-alkylene group which, if appropriate, has one or more substituents which are $C_1$-$C_4$-alkyl groups, or are $C_1$-$C_4$-alkoxy groups, and/or are halogen atoms, preferably chlorine atoms. Merely by way of example, mention may be made of ethylene oxide, propylene 1,2-oxide, butylene 1,2-oxide, butylene 1,3-oxide, 1,3-dioxane, 1,3-dioxolane, and 1,3-dioxepan as cyclic ethers, and also of linear oligo- or polyformals, such as polydioxolane or polydioxepan, as comonomers. It is particularly advantageous to use copolymers composed of from 99.5 to 95 mol. % of trioxane and of from 0.01 to 5 mol. %, such as from 0.5 to 4 mol. %, of one of the above-mentioned comonomers. In one embodiment, the polyoxymethylene polymer contains relatively low amounts of comonomer. For instance, the comonomer can be present in an amount less than about 2 mol. %, such as less than about 1.5 mol. %, such as less than about 1 mol. %, such as less than about 0.8 mol. %, such as less than about 0.6 mol. %.

The polymerization can be effected as precipitation polymerization or in the melt. By a suitable choice of the polymerization parameters, such as duration of polymerization or amount of molecular weight regulator, the molecular weight and hence the MVR value of the resulting polymer can be adjusted.

In one embodiment, the polyoxymethylene polymer used in the polymer composition may contain a relatively high amount of reactive groups or functional groups in the terminal positions. The reactive groups, for instance, may comprise —OH or —NH$_2$ groups.

In one embodiment, the polyoxymethylene polymer can have terminal hydroxyl groups, for example hydroxyethylene groups and/or hydroxyl side groups, in at least more than about 50% of all the terminal sites on the polymer. For instance, the polyoxymethylene polymer may have at least about 70%, such as at least about 80%, such as at least about 85% of its terminal groups be hydroxyl groups, based on the total number of terminal groups present. It should be understood that the total number of terminal groups present includes all side terminal groups.

In one embodiment, the polyoxymethylene polymer has a content of terminal hydroxyl groups of at least 15 mmol/kg, such as at least 18 mmol/kg, such as at least 20 mmol/kg. In one embodiment, the terminal hydroxyl group content ranges from 18 to 50 mmol/kg. In an alternative embodiment, the polyoxymethylene polymer may contain terminal hydroxyl groups in an amount less than 20 mmol/kg, such as less than 18 mmol/kg, such as less than 15 mmol/kg. For instance, the polyoxymethylene polymer may contain terminal hydroxyl groups in an amount from about 5 mmol/kg to about 20 mmol/kg, such as from about 5 mmol/kg to about 15 mmol/kg. For example, a polyoxymethylene polymer may be used that has a lower terminal hydroxyl group content but has a higher melt volume flow rate.

In addition to or instead of the terminal hydroxyl groups, the polyoxymethylene polymer may also have other terminal groups usual for these polymers. Examples of these are alkoxy groups, formate groups, acetate groups or aldehyde groups. According to one embodiment, the polyoxymethylene is a homo- or copolymer which comprises at least 50 mol-%, such as at least 75 mol-%, such as at least 90 mol-% and such as even at least 95 mol-% of —CH$_2$O— repeat units.

In one embodiment, a polyoxymethylene polymer can be produced using a cationic polymerization process followed by solution hydrolysis to remove any unstable end groups. During cationic polymerization, a glycol, such as ethylene glycol or methylal can be used as a chain terminating agent. A heteropoly acid, triflic acid or a boron compound may be used as the catalyst.

The polyoxymethylene polymer can have any suitable molecular weight. The molecular weight of the polymer, for instance, can be from about 4,000 grams per mole to about 20,000 g/mol. In other embodiments, however, the molecular weight can be well above 20,000 g/mol, such as from about 20,000 g/mol to about 100,000 g/mol.

The polyoxymethylene polymer present in the composition can generally have a melt flow index (MFI) ranging from about 0.1 to about 80 cm$^3$/10 min, as determined according to ISO 1133 at 190° C. and 2.16 kg. In one embodiment, the polyoxymethylene polymer may have a melt flow index of greater than about 1 cm$^3$/10 min, such as greater than about 2 cm$^3$/10 min, such as greater than about 5 cm$^3$/10 min, such as greater than about 10 cm$^3$/10 min, such as greater than about 20 cm$^3$/10 min, such as greater than about 30 cm$^3$/10 min. The polymer may, in some cases, have a melt flow index of less than about 55 cm$^3$/10 min, such as less than about 45 cm$^3$/10 min, such as less than about 35 cm$^3$/10 min, such as less than about 25 cm$^3$/10 min, such as less than about 15 cm$^3$/10 min, such as less than about 10 cm$^3$/10 min, such as less than about 5 cm$^3$/10 min.

The polyoxymethylene polymer may be present in the polymer composition in an amount of at least about 40% by weight, such as in an amount of at least about 50% by weight, such as in an amount of at least about 60% by weight. The polyoxymethylene polymer is generally present in the polymer composition in an amount less than about 80% by weight, such as in an amount less than about 70% by weight, such as in an amount less than about 60% by weight.

Reinforcing Fibers

The polymer composition can optionally contain reinforcing fibers in addition to the thermoplastic polymer matrix. Thermoplastic polymers, such as polyester and polyoxymethylene polymers, are combined with fibrous fillers in order to increase the modulus and/or tensile strength of parts and products made from the reinforced composition. Problems have been experienced in the past, however, in incorporating reinforcing fibers into a polymer matrix that has the desired balance of properties. For instance, polymer composites containing reinforcing fibers may have adequate strength properties but can experience an increase in surface friction when moved across an adjacent surface. The increase in friction, for instance, can cause abrasive wear after extended periods of use. These problems can become exacerbated when a first part made from the polymer matrix is designed to slide or rub against an adjacent part made from the same reinforced polymer matrix.

In order to decrease the coefficient of friction of fiber reinforced polymers, various different tribological additives have been proposed for blending with the thermoplastic polymer and reinforcing fibers. The tribological additives can lower both friction and wear characteristics when the polymer composition is molded into a part and used in applications where the part contacts and slides against an adjacent surface. The multiple components contained in the polymer composition, however, can create problems during the molding process, especially during injection molding processes. For instance, many fiber reinforced polymer compositions have a tendency to create mold deposits that require periodic tool cleaning. Mold cleaning processes are not only time consuming but create delays in the production process.

In addition to creating mold deposits, fiber reinforced polymer compositions can also require relatively high ejection forces necessary in order to remove a part from a mold. Greater forces needed to remove parts can lead to part failure and can increase the accumulation of mold deposits.

In accordance with the present disclosure, however, reinforcing fibers can be incorporated into the polymer composition while minimizing mold deposits and reducing forces needed to remove parts from the mold by incorporating into the composition one or more mold release agents alone or in combination with the nucleant.

Reinforcing fibers of which use may advantageously be made are mineral fibers, such as glass fibers, polymer fibers, in particular organic high-modulus fibers, such as aramid fibers, or metal fibers, such as steel fibers, or carbon fibers or natural fibers, fibers from renewable resources.

These fibers may be in modified or unmodified form, e.g. provided with a sizing, or chemically treated, in order to improve adhesion to the plastic. Glass fibers are particularly preferred.

Glass fibers are provided with a sizing to protect the glass fiber, to smooth the fiber but also to improve the adhesion between the fiber and the matrix material. A sizing usually comprises silanes, film forming agents, lubricants, wetting agents, adhesive agents optionally antistatic agents and plasticizers, emulsifiers and optionally further additives.

Specific examples of silanes are aminosilanes, e.g. 3-trimethoxysilylpropylamine, N-(2-aminoethyl)-3-aminopropyltrimethoxy-silane, N-(3-trimethoxysilanylpropyl)ethane-1,2-diamine, 3-(2-aminoethyl-amino)propyltrimethoxysilane, N-[3-(trimethoxysilyl)propyl]-1,2-ethane-diamine.

Film forming agents are for example polyvinylacetates, polyesters and polyurethanes. Sizings based on polyurethanes may be used advantageously.

The reinforcing fibers may be compounded into the polymer matrix, for example in an extruder or kneader.

According to one embodiment, the molding composition of the present disclosure comprises at least one reinforcing fiber which is a mineral fiber, preferably a glass fiber, more preferably a coated or impregnated glass fiber. Glass fibers which are suitable for the molding composition of the present disclosure are commercially available, e.g. Johns Manville, ThermoFlow®Chopped Strand 753, OCV Chopped Strand 408 A, Nippon Electric Glass Co. (NEG) Chopped Strand T-651.

Fiber diameters can vary depending upon the particular fiber used and whether the fiber is in either a chopped or a continuous form. The fibers, for instance, can have a diameter of from about 5 μm to about 100 μm, such as from about 5 μm to about 50 μm, such as from about 5 μm to about 15 μm. The length of the fibers can vary depending upon the particular application. For instance, the fibers can have a length of greater than about 100 microns, such as greater than about 200 microns, such as greater than about 300 microns, such as greater than about 350 microns. The length of the fibers can generally be less than about 1,000 microns, such as less than about 800 microns, such as less than about 600 microns, such as less than about 500 microns. Once incorporated into the polymer composition and molded into an article, the fiber length can decrease. For instance, the average fiber length in the final product can be from about 100 microns to about 400 microns, such as from about 100 microns to about 300 microns.

In general, reinforcing fibers can be present in the polymer composition in amounts sufficient to increase the tensile strength of the composition. The reinforcing fibers, for example, can be present in the polymer composition in an amount greater than about 5% by weight, such as in an amount greater than about 10% by weight, such as in an amount greater than about 15% by weight, such as in an amount greater than about 20% by weight, such as in an amount greater than about 25% by weight, such as in an amount greater than about 30% by weight. The reinforcing fibers are generally present in an amount less than about 55% by weight, such as in an amount less than about 50% by weight, such as in an amount less than about 45% by weight, such as in an amount less than about 40% by weight, such as in an amount less than about 35% by weight, such as in an amount less than about 30% by weight.

Mold Release Agent

In accordance with the present disclosure, the polymer composition contains one or more mold release agents that are added in an amount sufficient to lower ejection forces of parts from a mold, such as a mold during injection molding. Alternatively, the one or more mold release agents can be added in an amount sufficient to lower mold deposits, in comparison to an identical composition not containing the one or more mold release agents.

In one aspect, the one or more mold release agents alone or in combination with a nucleant can improve the melt processing behavior or properties of the polymer composition. The mold release package of the present disclosure, for instance, can increase crystallization rates and melt-solidification rates. Polymer compositions incorporating the mold release package can also form a more stable melt that can significantly improve cycle times and increase production.

In one aspect, the polymer composition only contains a single mold release agent. The mold release agent, for instance, can be a polar mold release agent and/or an oxidized mold release agent. Polar materials, for instance, blend well with the other components. The polar polymers for use in the present disclosure have been found to dramatically reduce mold deposits due to their interactions with the other components during molding. The polar mold release agent, for instance, can be an oxidized wax, such as an oxidized polyolefin wax or oxidized esters of carboxylic acids. The oxidized polyolefin wax, for instance, can be an oxidized polyethylene wax.

The polarity of the mold release agent can vary depending upon the particular application and the desired result. The polarity, for instance, can be indicated by the acid value of the mold release agent. The acid value of the polar mold release agent, for instance, can generally be greater than about 10 KOH/g, such as greater than about 15 KOH/g, such as greater than about 20 KOH/g, such as greater than about 25 KOH/g, such as greater than about 30 KOH/g, such as greater than about 35 KOH/g, such as greater than about 40 KOH/g, such as greater than about 45 KOH/g, such as greater than about 50 KOH/g. The acid value is generally less than about 95 KOH/g, such as less than about 90 KOH/g, such as less than about 85 KOH/g, such as less than about 80 KOH/g, such as less than about 75 KOH/g, such as less than about 70 KOH/g.

In one aspect, the acid value of the polar mold release agent can be from about 13 KOH/g to about 23 KOH/g, such as from about 15 KOH/g to about 19 KOH/g. In an alternative embodiment, the acid value of the polar mold release agent can be from about 40 KOH/g to about 65 KOH/g, such as from about 45 KOH/g to about 55 KOH/g.

As described above, in one embodiment, the polar mold release agent can be oxidized esters of carboxylic acids. In one aspect, the oxidized esters of carboxylic acids can be derived from biomass materials, such as rice bran.

The different carboxylic acids used to produce the oxidized esters of fatty acids can vary depending upon the source of the fatty acids and the desired result. In one embodiment, the oxidized esters of fatty acids can be derived from at least three different fatty acids, such as at least five different fatty acids, such as at least about eight different fatty acids, and generally less than about 20 different fatty acids, such as less than about 15 different fatty acids. The fatty acids used to produce the oxidized esters, for instance, can have various different chain lengths. For instance, of all the fatty acids present in the oxidized wax, greater than about 20% by weight, such as greater than about 30% by weight, such as greater than about 40% by weight, such as greater than about 50% by weight, such as greater than about 60% by weight, can be derived from fatty acids having a carbon chain length of from about 20 carbon atoms to about 40 carbon atoms. The oxidized wax can also be derived from longer chain fatty acids. For instance, the oxidized wax can be derived from greater than about 5% by weight, such as greater than about 10% by weight, such as greater than about 15% by weight, such as greater than about 20% by weight, such as greater than about 25% by weight, such as greater than about 30% by weight, such as greater than about 40% by weight, such as greater than about 45% by weight, such as greater than about 50% by weight of fatty acids having a carbon chain length of from about 40 carbon atoms to about 64 carbon atoms. The above carboxylic acids can be aliphatic carboxylic acids. In one aspect, the oxidized wax contains less than about 5% by weight of esters derived from fatty acids having a carbon chain length of less than about 14 carbon atoms, such as less than about 12 carbon atoms, such as less than about 10 carbon atoms, such as less than about 8 carbon atoms.

In one particular embodiment, the polymer composition contains a first mold release agent and a second mold release agent that are both completely safe for food handling applications and/or medical applications. The first mold release agent, for instance, can be a polar polymer.

Various different polar materials may be used as the first mold release agent, including the polar polymers described above. The polar polymer, for instance, can be a polyolefin polymer, particularly a modified polyolefin polymer. The polar, polyolefin polymer, for instance, can be a polyethylene polymer or a polypropylene polymer, including copolymers thereof. In one particular embodiment, the first mold release agent can be an oxidized polyethylene wax.

Other polar waxes can be polar-modified polymers of ethylene and/or propylene formed using, for example, metallocene catalysts. Examples that can be mentioned include homopolymers or copolymers of ethylene and/or propylene modified in the presence of hydrophilic groups such as maleic anhydride, acrylate, methacrylate, or polyvinylpyrrolidone (PVP) groups. Examples include maleic anhydride modified polypropylene polymers (PPMA), or maleic anhydride polypropylene and ethylene copolymers. In one aspect, the polar wax can be derived from rice bran as described above.

In addition to polar materials, effective mold release agents can also comprise non-polar materials, such as non-polar polymers. Non-polar polymers, for example, can migrate to the surface of polymer articles made from the polymer composition during molding. In this manner, non-polar polymer materials in accordance with the present disclosure can significantly reduce the amount of force needed in order to eject a part from a mold. Non-polar polymers that may be used in accordance with the present disclosure include various different non-polar polyolefin polymers, including polyethylene polymers and polypropylene polymers. The polyolefin polymer can be a homopolymer or a copolymer. In one embodiment, the non-polar polymer can be a polyethylene wax.

In one particular embodiment, the polymer composition contains a first mold release agent comprising a polar polymer in combination with a second mold release agent comprising a non-polar polymer.

Each mold release agent can be present in the polymer composition generally in an amount less than about 2% by weight, such as in an amount less than about 1% by weight, such as in an amount less than about 0.8% by weight, such as in an amount less than about 0.6% by weight, such as in an amount less than about 0.4% by weight, such as in an amount less than about 0.2% by weight. The one or more mold release agents are generally present in the polymer composition in an amount greater than about 0.01% by weight.

When the polymer composition contains a first mold release agent in combination with a second mold release agent as described above, the weight ratio between the first mold release agent and the second mold release agent can be from about 10:1 to about 1:10, such as from about 5:1 to about 1:5, such as from about 2:1 to about 1:2.

Tribological Modifier

According to the present disclosure, the polymer composition and the polymer article comprising the reinforced polymer composition may comprise at least one tribological modifier.

In one embodiment, ultra-high molecular weight silicone (UHMW-Si) may be used to modify the thermoplastic polymer. In general, the UHMW-Si can have an average molecular weight of greater than 100,000 g/mol, such as greater than about 200,000 g/mol, such as greater than about 300,000 g/mol, such as greater than about 500,000 g/mol and less than about 3,000,000 g/mol, such as less than about 2,000,000 g/mol, such as less than about 1,000,000 g/mol, such as less than about 500,000 g/mol, such as less than about 300,000 g/mol. Generally, the UHMW-Si can have a kinematic viscosity at 40° C. measured according to DIN 51562 of greater than 100,000 mm$^2$ s$^{-1}$, such as greater than about 200,000 mm$^2$ s$^{-1}$, such as greater than about 1,000,000 mm$^2$ s$^{-1}$, such as greater than about 5,000,000 mm$^2$ s$^{-1}$, such as greater than about 10,000,000 mm$^2$ s$^{-1}$, such as greater than about 15,000,000 mm$^2$ s$^{-1}$ and less than about 50,000,000 mm$^2$ s$^{-1}$, such as less than about 25,000,000 mm$^2$ s$^{-1}$, such as less than about 10,000,000 mm$^2$ s$^{-1}$, such as less than about 1,000,000 mm$^2$ s$^{-1}$, such as less than about 500,000 mm$^2$ s$^{-1}$, such as less than about 200,000 mm$^2$ s$^{-1}$.

The UHMW-Silicone may comprise a siloxane such as a polysiloxane or polyorganosiloxane. In one embodiment, the UHMW-Si may comprise a dialkylpolysiloxane such as a dimethylsiloxane, an alkylarylsiloxane such as a phenylmethylsiloxane, a polysilsesquioxane, or a diarylsiloxane such as a diphenylsiloxane, or a homopolymer thereof such as a polydimethylsiloxane or a polymethylphenylsiloxane, or a copolymer thereof with the above molecular weight and/or kinematic viscosity requirements. The polysiloxane or polyorganosiloxane may also be modified with a substituent such as an epoxy group, a hydroxyl group, a carboxyl group, an amino group or a substituted amino group, an ether group, or a meth(acryloyl) group in the end or main chain of the molecule. The UHMW-Si compounds may be used singly or in combination. Any of the above UHMW-Si compounds may be used with the above molecular weight and/or kinematic viscosity requirements.

The UHMW-Silicone may be added to the polymer composition as a masterbatch wherein the UHMW-Si is dispersed in a carrier polymer and the masterbatch is thereafter added to the composition. The masterbatch may comprise from about 10 wt. % to about 60 wt. %, such as from about 35 wt. % to about 55 wt. %, such as about 50 wt. % of an UHMW-Si.

The carrier polymer can vary depending upon the particular application and the desired result. In one embodiment, for instance, the carrier polymer may comprise a polyester polymer. The polyester carrier polymer, for instance, may comprise polybutylene terephthalate, polyethylene terephthalate, a copolyester, and/or a polyester elastomer. The polyester elastomer may comprise a copolyester such as a segmented thermoplastic copolyester. The polyester elastomer, for example, may comprise a multi-block copolymer.

The UHMW-Silicone may be present in the polymer composition in an amount of at greater than about 0.005 wt. %, such as at greater than about 0.1 wt. %, such as at greater than about 0.5 wt. %, such as at greater than about 0.75 wt. %, such as at greater than about 1 wt. %, such as at greater than about 2 wt. %, such as at greater than about 2.5 wt. % and generally less than about 10 wt. %, such as less than about 6 wt. %, such as less than about 5 wt. %, such as less than about 4 wt. %, such as less than about 3.5 wt. %, such as less than about 3 wt. %, wherein the weight is based on the total weight of the polymer composition.

In an alternative embodiment, the at least one tribological additive may comprise a fluoropolymer, such as polytetrafluoroethylene powder. The fluoropolymer may be combined with the ultra-high molecular weight silicone in one application. The polytetrafluoroethylene particles, for instance, can have an average particle size of less than about 15 microns, such as less than about 12 microns, such as less than about 10 microns, such as less than about 8 microns. The average particle size of the polytetrafluoroethylene particles is generally greater than about 0.5 microns, such as greater than about 1 micron, such as greater than about 2 microns, such as greater than about 3 microns, such as greater than about 4 microns, such as greater than about 5 microns. Average particle size can be measured according to ISO Test 13321.

In one embodiment, the polytetrafluoroethylene particles can have a relatively low molecular weight. The polytetrafluoroethylene polymer may have a density of from about 300 g/l to about 450 g/l, such as from about 325 g/l to about 375 g/l when tested according to ASTM Test D4895. The polytetrafluoroethylene particles can have a specific surface area of from about 5 m$^2$/g to about 15 m$^2$/g, such as from about 8 m$^2$/g to about 12 m$^2$/g when tested according to Test DIN66132. The melt flow rate of the polytetrafluoroethylene polymer can be less than about 3 g/10 min, such as less than about 2 g/10 min when tested according to ISO Test 1133 when carried out at 372° C. with a load of 10 kg.

The polytetrafluoroethylene particles can be present in the polymer composition in an amount greater than about 1% by weight, such as in an amount greater than about 2% by weight, such as in an amount greater than about 3% by weight, such as in an amount greater than about 4% by weight. The polytetrafluoroethylene polymer is generally present in the polymer composition in an amount less than about 20% by weight, such as in an amount less than about 15% by weight, such as in an amount less than about 10% by weight, such as in an amount less than about 8% by weight.

Other Additives

The polymer composition of the present disclosure can contain various other additives. For example, the composition may further include a nucleant present in a concentration of between about 0.1 and 2% by weight, preferably between about 0.001% and 0.5% based on the total weight of the composition. The nucleant can be selected from the group consisting of alkali metal salts having anions which are oxides of the elements from Group IV of the Periodic Table; barium sulfate; and talc.

The polymer composition may also contain at least one stabilizer. The stabilizer may comprise an antioxidant, a light stabilizer such as an ultraviolet light stabilizer, a thermal stabilizer, and the like.

Sterically hindered phenolic antioxidant(s) may be employed in the composition. Examples of such phenolic antioxidants include, for instance, calcium bis(ethyl 3,5-di-tert-butyl-4-hydroxybenzylphosphonate) (Irganox® 1425); terephthalic acid, 1,4-dithio-,S,S-bis(4-tert-butyl-3-hydroxy-2,6-dimethylbenzyl) ester (Cyanox® 1729); triethylene glycol bis(3-tert-butyl-4-hydroxy-5-methylhydrocinnamate); hexamethylene bis(3,5-di-tert-butyl-4-hydroxyhydrocinnamate (Irganox® 259); 1,2-bis(3,5-di-tert-butyl-4-hydroxyhydrocinnamoyl)hydrazide (Irganox® 1024); 4,4'-di-tert-octyldiphenamine (Naugalube® 438R); phosphonic acid, (3,5-di-tert-butyl-4-hydroxybenzyl)-, dioctadecyl ester (Irganox® 1093); 1,3,5-trimethyl-2,4,6-tris(3',5'-di-tert-butyl-4' hydroxybenzyl)benzene (Irganox® 1330); 2,4-bis(octylthio)-6-(4-hydroxy-3,5-di-tert-butylanilino)-1,3,5-triazine (Irganox® 565); isooctyl 3-(3,5-di-tert-butyl-4-hydroxyphenyl)propionate (Irganox® 1135); octadecyl 3-(3,5-di-tert-butyl-4-hydroxyphenyl)propionate (Irganox® 1076); 3,7-bis(1,1,3,3-tetramethylbutyl)-10H-phenothiazine (Irganox® LO 3); 2,2'-methylenebis(4-methyl-6-tert-butylphenol)monoacrylate (Irganox® 3052); 2-tert-butyl-6-[1-(3-tert-butyl-2-hydroxy-5-methylphenyl)ethyl]-4-methylphenyl acrylate (Sumilizer™ 4039); 2-[1-(2-hydroxy-3,5-di-tert-pentylphenyl)ethyl]-4,6-di-tert-pentylphenyl acrylate (Sumilizer® GS); 1,3-dihydro-2H-Benzimidazole (Sumilizer® MB); 2-methyl-4,6-bis[(octylthio)methyl]phenol (Irganox® 1520); N,N'-trimethylenebis-[3-(3,5-di-tert-butyl-4-hydroxyphenyl) propionamide (Irganox® 1019); 4-n-octadecyloxy-2,6-diphenylphenol (Irganox® 1063); 2,2'-ethylidenebis[4,6-di-tert-butylphenol] (Irganox® 129); N,N'-hexamethylenebis (3,5-di-tert-butyl-4-hydroxyhydrocinnamamide) (Irganox® 1098); diethyl (3,5-di-tert-butyl-4-hydroxybenxyl)phosphonate (Irganox® 1222); 4,4'-di-tert-octyldiphenylamine (Irganox® 5057); N-phenyl-1-napthalenamine (Irganox® L 05); tris[2-tert-butyl-4-(3-ter-butyl-4-hydroxy-6-methylphenylthio)-5-methyl phenyl]phosphite (Hostanox® OSP 1); zinc dinonyidithiocarbamate (Hostanox® VP-ZNCS 1); 3,9-bis(1,1-diimethyl-2-[(3-tert-butyl-4-hydroxy-5-methylphenyl)propionyloxy]ethyl]-2,4,8,10-tetraoxaspiro[5.5]undecane (Sumilizer® AG80); pentaerythrityl tetrakis[3-(3,5-di-tert-butyl-4-hydroxyphenyl)propionate] (Irganox® 1010); ethylene-bis(oxyethylene)bis[3-(5-tert-butyl-4-hydroxy-m-tolyl)-propionate (Irganox® 245); 3,5-di-tert-butyl-4-hydroxytoluene (Lowinox BHT, Chemtura) and so forth.

Some examples of suitable sterically hindered phenolic antioxidants for use in the present composition are triazine antioxidants having the following general formula:

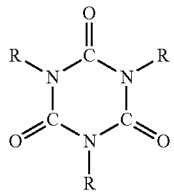

wherein, each R is independently a phenolic group, which may be attached to the triazine ring via a $C_1$ to $C_5$ alkyl or an ester substituent. Preferably, each R is one of the following formula (I)-(III):

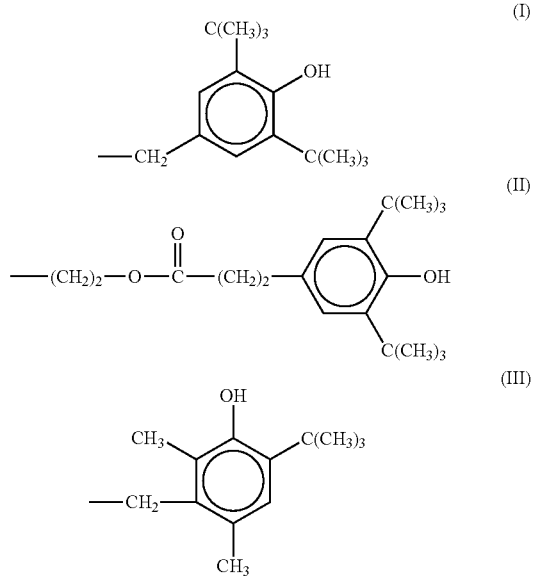

Commercially available examples of such triazine-based antioxidants may be obtained from American Cyanamid under the designation Cyanox® 1790 (wherein each R group is represented by the Formula III) and from Ciba Specialty Chemicals under the designations Irganox® 3114 (wherein each R group is represented by the Formula I) and Irganox® 3125 (wherein each R group is represented by the Formula II).

Sterically hindered phenolic antioxidants may constitute from about 0.01 wt. % to about 3 wt. %, in some embodiments from about 0.05 wt. % to about 1 wt. %, and in some embodiments, from about 0.05 wt. % to about 0.1 wt. % of the entire stabilized polymer composition. In one embodiment, for instance, the antioxidant comprises pentaerythrityl tetrakis[3-(3,5-di-tert-butyl-4-hydroxyphenyl)propionate.

Hindered amine light stabilizers ("HALS") may be employed in the composition to inhibit degradation of the polymer composition and thus extend its durability. Suitable HALS compounds may be derived from a substituted piperidine, such as alkyl-substituted piperidyl, piperidinyl, piperazinone, alkoxypiperidinyl compounds, and so forth. For example, the hindered amine may be derived from a 2,2,6,6-tetraalkylpiperidinyl. Regardless of the compound from which it is derived, the hindered amine is typically an oligomeric or polymeric compound having a number average molecular weight of about 1,000 or more, in some embodiments from about 1000 to about 20,000, in some embodiments from about 1500 to about 15,000, and in some embodiments, from about 2000 to about 5000. Such compounds typically contain at least one 2,2,6,6-tetraalkylpiperidinyl group (e.g., 1 to 4) per polymer repeating unit.

Without intending to be limited by theory, it is believed that high molecular weight hindered amines are relatively thermostable and thus able to inhibit light degradation even after being subjected to extrusion conditions. One particularly suitable high molecular weight hindered amine has the following general structure:

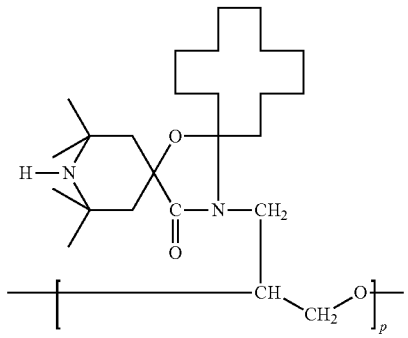

wherein, p is 4 to 30, in some embodiments 4 to 20, and in some embodiments 4 to 10. This oligomeric compound is commercially available from Clariant under the designation Hostavin® N30 and has a number average molecular weight of 1200.

Another suitable high molecular weight hindered amine has the following structure:

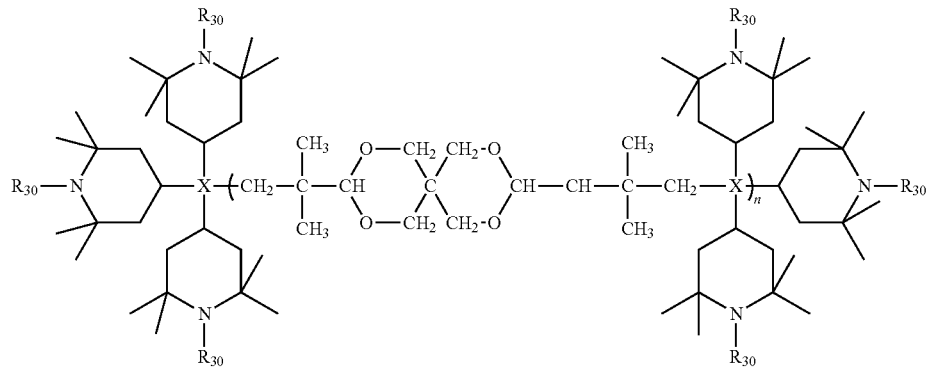

wherein, n is from 1 to 4 and $R_{30}$ is independently hydrogen or $CH_3$. Such oligomeric compounds are commercially available from Adeka Palmarole SAS (joint venture between Adeka Corp. and Palmarole Group) under the designation ADK STAB® LA-63 ($R_{30}$ is $CH_3$) and ADK STAB® LA-68 ($R_{30}$ is hydrogen).

Other examples of suitable high molecular weight hindered amines include, for instance, an oligomer of N-(2-hydroxyethyl)-2,2,6,6-tetramethyl-4-piperidinol and succinic acid (Tinuvin® 622 from Ciba Specialty Chemicals, MW=4000); oligomer of cyanuric acid and N,N-di(2,2,6,6-tetramethyl-4-piperidyl)-hexamethylene diamine; poly((6-morpholine-S-triazine-2,4-diyl)(2,2,6,6-tetramethyl-4-piperidinyl)-iminohexamethylene-(2,2,6,6-tetramethyl-4-piperidinyl)-imino) (Cyasorb® UV 3346 from Cytec, MW=1600); polymethylpropyl-3-oxy-[4(2,2,6,6-tetramethyl)-piperidinylysiloxane (Uvasil® 299 from Great Lakes Chemical; MW=1100 to 2500); copolymer of α-methylstyrene-N-(2,2,6,6-tetramethyl-4-piperidinyl)maleimide and N-stearyl maleimide; 2,4,8,10-tetraoxaspiro[5.5]undecane-3,9-diethanol tetramethyl-polymer with 1,2,3,4-butanetetracarboxylic acid; and so forth. Still other suitable high molecular weight hindered amines are described in U.S. Pat. No. 5,679,733 to Malik, et al. and U.S. Pat. No. 6,414,155 to Sassi, et al., which are incorporated herein in their entirety by reference thereto for all purposes.

In addition to the high molecular hindered amines, low molecular weight hindered amines may also be employed in the composition. Such hindered amines are generally monomeric in nature and have a molecular weight of about 1000 or less, in some embodiments from about 155 to about 800, and in some embodiments, from about 300 to about 800.

Specific examples of such low molecular weight hindered amines may include, for instance, bis-(2,2,6,6-tetramethyl-4-piperidyl) sebacate (Tinuvin® 770 from Ciba Specialty Chemicals, MW=481); bis-(1,2,2,6,6-pentamethyl-4-piperidinyl)-(3,5-ditert.butyl-4-hydroxybenzyl)butyl-propane dioate; bis-(1,2,2,6,6-pentamethyl-4-piperidinyl)sebacate; 8-acetyl-3-dodecyl-7,7,9,9-tetramethyl-1,3,8-triazaspiro-(4,5)-decane-2,4-dione, butanedioic acid-bis-(2,2,6,6-tetramethyl-4-piperidinyl) ester; tetrakis-(2,2,6,6-tetramethyl-4-piperidyl)-1,2,3,4-butane tetracarboxylate; 7-oxa-3,20-diazadispiro(5.1.11.2) heneicosan-20-propanoic acid, 2,2,4,4-tetramethyl-21-oxo, dodecyl ester; N-(2,2,6,6-tetramethyl-4-piperidinyl)-N'-amino-oxamide; o-t-amyl-o-(1,2,2,6,6-pentamethyl-4-piperidinyl)-monoperoxicarbonate; β-alanine, N-(2,2,6,6-tetramethyl-4-piperidinyl), dodecylester; ethanediamide, N-(1-acetyl-2,2,6,6-tetramethylpiperidinyl)-N'-dodecyl; 3-dodecyl-1-(2,2,6,6-tetramethyl-4-piperidinyl)-pyrrolidin-2,5-dione; 3-dodecyl-1-(1,2,2,6,6-pentamethyl-4-piperidinyl)-pyrrolidin-2,5-dione; 3-dodecyl-1-(1-acetyl,2,2,6,6-tetramethyl-4-piperidinyl)-pyrrolidin-2,5-dione, (Sanduvar® 3058 from Clariant, MW=448.7); 4-benzoyloxy-2,2,6,6-tetramethylpiperidine; 1-[2-(3,5-di-tert-butyl-4-hydroxyphenylpropionyloxy) ethyl]-4-(3,5-di-tert-butyl-4-hydroxylphenyl propionyloxy)-2,2,6,6-tetramethyl-piperidine; 2-methyl-2-(2″,2″,6″,6″-tetramethyl-4″-piperidinylamino)-N-(2′,2′,6′,6′-tetra-methyl-4″-piperidinyl)propionylamide; 1,2-bis-(3,3,5,5-tetramethyl-2-oxo-piperazinyl)ethane; 4-oleoyloxy-2,2,6,6-tetramethylpiperidine, and combinations thereof. Other suitable low molecular weight hindered amines are described in U.S. Pat. No. 5,679,733 to Malik, et al.

The hindered amines may be employed singularly or in combination in any amount to achieve the desired properties, but typically constitute from about 0.01 wt. % to about 4 wt. % of the polymer composition.

UV absorbers, such as benzotriazoles or benzopheones, may be employed in the composition to absorb ultraviolet light energy. Suitable benzotriazoles may include, for instance, 2-(2-hydroxyphenyl)benzotriazoles, such as 2-(2-hydroxy-5-methylphenyl)benzotriazole; 2-(2-hydroxy-5-tert-octylphenyl)benzotriazole (Cyasorb® UV 5411 from Cytec); 2-(2-hydroxy-3,5-di-tert-butylphenyl)-5-chlorobenzo-triazole; 2-(2-hydroxy-3-tert-butyl-5-methylphenyl)-5-chlorobenzotriazole; 2-(2-hydroxy-3,5-dicumylphenyl)benzotriazole; 2,2'-methylenebis(4-tert-octyl-6-benzotriazolylphenol); polyethylene glycol ester of 2-(2-hydroxy-3-tert-butyl-5-carboxyphenyl)benzotriazole; 2-[2-hydroxy-3-(2-acryloyloxyethyl)-5-methylphenyl]-benzotriazole; 2-[2-hydroxy-3-(2-methacryloyloxyethyl)-5-tert-butylphenyl]benzotriazole; 2-[2-hydroxy-3-(2-methacryloyloxyethyl)-5-tert-octylphenyl]benzotriazole; 2-[2-hydroxy-3-(2-methacryloyloxyethyl)-5-tert-butylphenyl]-5-chlorobenzotriazole; 2-[2-hydroxy-5-(2-methacryloyloxyethyl)phenyl]benzotriazole; 2-[2-hydroxy-3-tert-butyl-5-(2-methacryloyloxyethyl)phenyl]benzotriazole; 2-[2-hydroxy-3-tert-amyl-5-(2-methacryloyloxyethyl)phenyl]benzotriazole; 2-[2-hydroxy-3-tert-butyl-5-(3-methacryloyloxypropyl)phenyl]-5-chlorobenzotriazole; 2-[2-hydroxy-4-(2-methacryloyloxymethyl)phenyl]enzotriazole; 2-[2-hydroxy-4-(3-methacryloyloxy-2-hydroxypropyl)phenyl] benzotriazole; 2-[2-hydroxy-4-(3-methacryloyloxypropyl) phenyl]benzotriazole; and combinations thereof.

Exemplary benzophenone light stabilizers may likewise include 2-hydroxy-4-dodecyloxybenzophenone; 2,4-dihydroxybenzophenone; 2-(4-benzoyl-3-hydroxyphenoxy) ethyl acrylate (Cyasorb® UV 209 from Cytec); 2-hydroxy-4-n-octyloxy)benzophenone (Cyasorb® 531 from Cytec); 2,2'-dihydroxy-4-(octyloxy)benzophenone (Cyasorb® UV 314 from Cytec); hexadecyl-3,5-bis-tert-butyl-4-hydroxybenzoate (Cyasorb® UV 2908 from Cytec); 2,2'-thiobis(4-tert-octylphenolato)-n-butylamine nickel(II) (Cyasorb® UV 1084 from Cytec); 3,5-di-tert-butyl-4-hydroxybenzoic acid, (2,4-di-tert-butylphenyl)ester (Cyasorb® 712 from Cytec); 4,4'-dimethoxy-2,2'-dihydroxybenzophenone (Cyasorb® UV 12 from Cytec); and combinations thereof.

When employed, UV absorbers may constitute from about 0.01 wt. % to about 4 wt. % of the entire polymer composition.

In one embodiment, the polymer composition may contain a blend of stabilizers that produce ultraviolet resistance and color stability. The combination of stabilizers may allow for products to be produced that have bright and fluorescent colors. In addition, bright colored products can be produced without experiencing significant color fading over time. In one embodiment, for instance, the polymer composition may contain a combination of a benzotriazole light stabilizer and a hindered amine light stabilizer, such as an oligomeric hindered amine.

In one embodiment, an amide wax may be present in the polymer composition. Amide waxes, for instance, may be employed that are formed by reaction of a fatty acid with a monoamine or diamine (e.g., ethylenediamine) having 2 to 18, especially 2 to 8, carbon atoms. For example, ethylenebisamide wax, which is formed by the amidization reaction of ethylene diamine and a fatty acid, may be employed. The fatty acid may be in the range from $C_{12}$ to $C_{30}$, such as from stearic acid ($C_{18}$ fatty acid) to form ethylenebisstearamide wax. Ethylenebisstearamide wax is commercially available from Lonza, Inc. under the designation Acrawax® C, which has a discrete melt temperature of 142° C. Other ethylenebisamides include the bisamides formed from lauric acid, palmitic acid, oleic acid, linoleic acid, linolenic acid, oleostearic acid, myristic acid and undecalinic acid. Still other suitable amide waxes are N-(2-hydroxyethy)12-hydroxystearamide and N,N'-(ethylene bis)12-hydroxystearamide.

In addition to the above components, the polymer composition may include various other ingredients. Colorants that may be used include any desired inorganic pigments, such as titanium dioxide, ultramarine blue, cobalt blue, and other organic pigments and dyes, such as phthalocyanines, anthraquinones, and the like. Other colorants include carbon black or various other polymer-soluble dyes. The colorants can generally be present in the composition in an amount up to about 2 percent by weight.

Polymer Articles

The compositions of the present disclosure can be compounded and formed into a polymer article using any technique known in the art. For instance, the respective composition can be intensively mixed to form a substantially homogeneous blend. The blend can be melt kneaded at an elevated temperature, such as a temperature that is higher than the melting point of the polymer utilized in the polymer composition but lower than the degradation temperature. Alternatively, the respective composition can be melted and mixed together in a conventional single or twin screw extruder. Preferably, the melt mixing is carried out at a temperature ranging from 150 to 300° C., such as from 200 to 280° C., such as from 220 to 270° C. or 240 to 260° C. However, such processing should be conducted for each respective composition at a desired temperature to minimize any polymer degradation.

After extrusion, the compositions may be formed into pellets. The pellets can be molded into polymer articles by techniques known in the art such as injection molding, thermoforming, blow molding, rotational molding and the like. According to the present disclosure, the polymer articles can demonstrate excellent tribological behavior and mechanical properties. Consequently, the polymer articles can be used for several applications where low wear and excellent gliding properties are desired.

Polymer articles include any moving articles or moldings that are in contact with another surface and may require high tribological requirements. For instance, polymer articles include articles for the automotive industry, especially housings, latches such as rotary latches, window winding systems, wiper systems, pulleys, sun roof systems, seat adjustments, levers, bushes, gears, gear boxes, claws, pivot housings, wiper arms, brackets or seat rail bearings, zippers, switches, cams, rollers or rolling guides, sliding elements or glides such as sliding plates, conveyor belt parts such as chain elements and links, castors, fasteners, levers, conveyor system wear strips and guard rails, medical devices such as medical inhalers, injection devices, surgical instruments, wearable devices and the like. An almost limitless variety of polymer articles may be formed from the polymer compositions of the present disclosure.

In one embodiment, the composition of the present disclosure is used to produce a first sliding member and a second sliding member. The first and second sliding members can both be made from a composition in accordance with the present disclosure. In particular, the first sliding member and the second sliding member can be made from a composition comprising a reinforced thermoplastic polymer in combination with one or more mold release agents and an ultrahigh molecular weight silicone. The relative amounts of the components can be the same or can be different in each composition.

The first sliding member and the second sliding member can be contained in an apparatus and placed in operative association with each other such that the sliding members move relative to each other. For instance, in one embodiment, the first sliding member may be stationary while the second sliding member moves across the first sliding member. Alternatively, both sliding members may move while contacting each other.

In one embodiment, the sliding members of the present disclosure can be used to produce a medical device. For instance, referring to FIG. 1, an inhaler 20 is shown. The inhaler 20 includes a housing 22 attached to a mouthpiece 24. In operative association with the housing 22 is a plunger 26 for receiving a canister containing a composition to be inhaled. The composition may comprise a spray or a powder. The inhaler 20 can include a first sliding member in operative association with a second sliding member. For instance, in certain embodiments, the housing 22 may comprise the first sliding member while the plunger 26 may comprise the second sliding member. Alternatively, the first sliding member may comprise the housing 22 and the second sliding member may comprise the mouthpiece 24. In still another embodiment, an internal sliding member may be contained within the housing 22 that slides relative to the housing.

During use, the inhaler 20 administers metered doses of a medication, such as an asthma medication to a patient. The asthma medication may be suspended or dissolved in a propellant or may be contained in a powder. When a patient actuates the inhaler to breathe in the medication, a valve opens allowing the medication to exit the mouthpiece.

Figure 2:
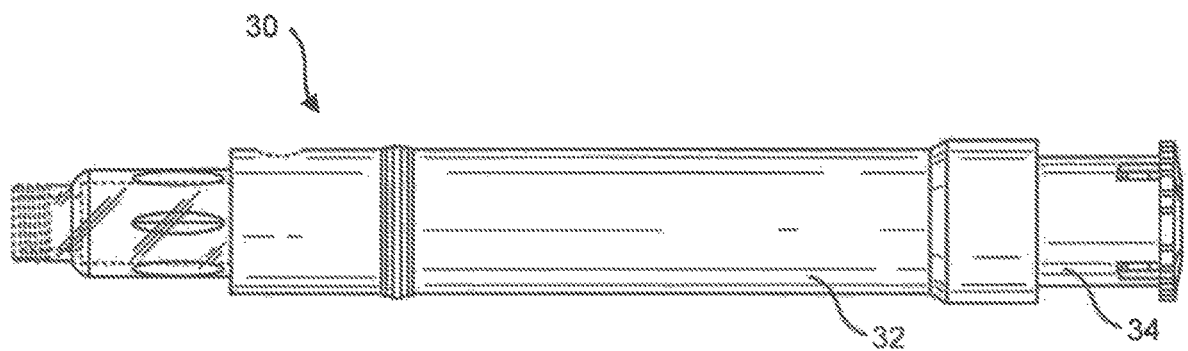
FIG. 2 is a side view of a medical injector that may be made in accordance with the present disclosure.
Figure 3:
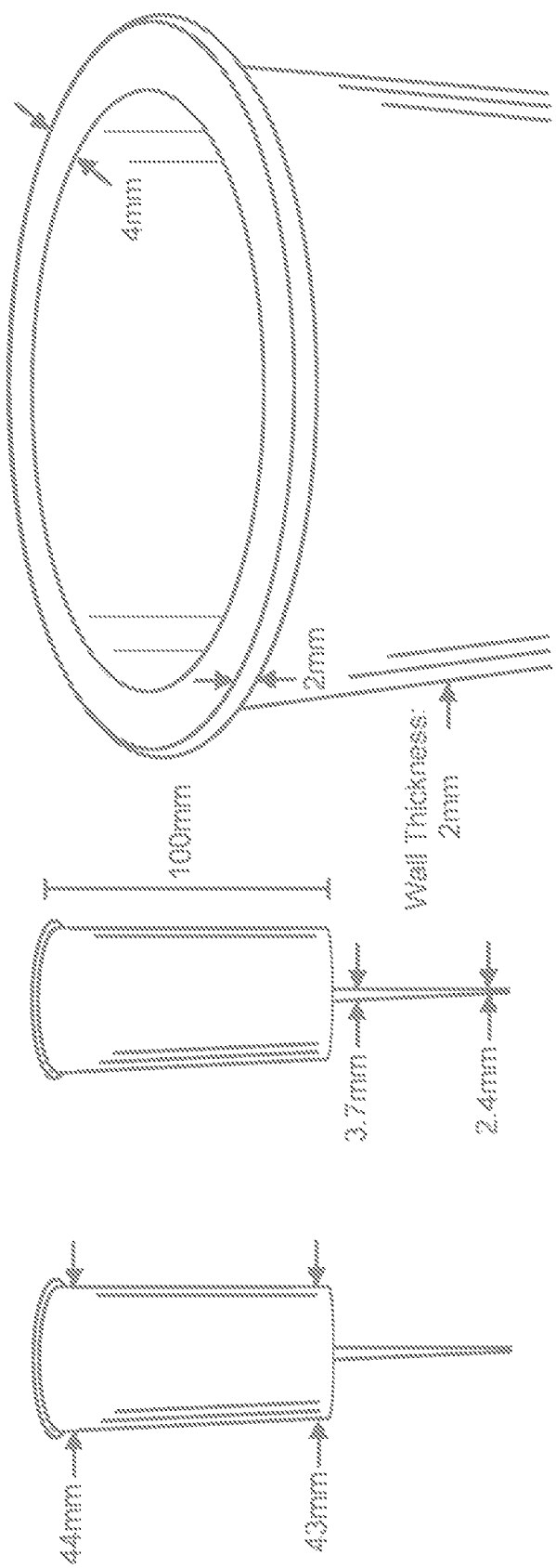
FIG. 3 is a perspective view of the dimensions of a molded article for use in conducting the part ejection test.

In another embodiment of the present disclosure, the first sliding member and the second sliding member are contained in a medical injector 30 as shown in FIG. 2. The medical injector 30 includes a housing 32 in operative association with a plunger 34. The housing 32 or first sliding member may slide relative to the plunger 34 or second sliding member. The medical injector 30 may be spring loaded. The medical injector 30 is for injecting a drug into a patient, typically into the thigh or the buttocks. The medical injector can be needleless or may contain a needle. When containing a needle, the needle tip is typically shielded within the housing prior to injection. Needleless injectors, on the other hand, can contain a cylinder of pressurized gas that propels a medication through the skin without the use of a needle.

The polymer composition of the present disclosure is particularly well suited to constructing injectors as shown in FIG. 2, including syringes and autoinjectors, for dispensing high viscosity medicaments, such as biologics including protein-based pharmaceuticals. As high viscosity medicaments have become more prevalent in the pharmaceutical pipeline, the delivery devices face various significant challenges that high-viscosity drugs present to traditional autoinjectors. The injectors, for instance, are formed with greater injection forces so as not to necessitate a larger diameter needle that can result in increased pain for the patient. These forces can be stored in the device, usually as a compressed spring, prior to actuation.

The polymer composition is not only well suited to producing high pressure delivery devices, but also can contribute to sustainability by being reusable and capable of being exposed to sterilization radiation without losing mechanical properties or accuracy. In particular, molded articles made according to the present disclosure are resistant to wear and creep, even after multiple uses.

Creep, or cold flow, refers to the tendency of materials to slowly deform when held under high stress for extended periods of time. As such, creep can be an important consideration when designing injectors for biologics. In order to deliver these viscous formulations without increasing the size of the needle, these injectors require greater force to push the drug through the needle than is typically required. As such, greater force needs to be stored within the device prior to actuation, usually in the form of a compressed spring. This means that the device components are going to be under greater stress and therefore more susceptible to creep and the loss of some of that stored force, which can compromise device reliability. Molded articles made according to the present disclosure have enhanced creep properties and other properties that make the articles well suited for the above application.

For example, in addition to excellent creep resistance, the polymer composition of the present disclosure exhibits retention of elongation suitable for snap-fit assembly, high strength and stiffness, excellent suitability for gamma sterilization, high wear-resistance, low breakaway force, soundless sliding and elimination of stick-slip for improved patient comfort during delivery, good chemical resistance, and a smooth, appealing surface finish.

In one aspect, the polymer composition of the present disclosure is used to produce an injector, particularly an autoinjector, that is designed to dispense high viscosity fluids, such as biologics. The biologics, for instance, can have a relatively high molecular weight. The biologics, for example, can have an average molecular weight of greater than about 50 kDa, such as greater than about 75 kDa, such as greater than about 100 kDa, such as greater than about 125 kDa. The above biologics can be contained in a fluid that has a viscosity of greater than about 7 cP, such as greater than about 10 cP, such as greater than about 12 cP, such as greater than about 15 cP, such as greater than about 20 cP, such as greater than about 25 cP, such as greater than about 50 cP, such as greater than about 75 cP, such as greater than about 100 cP, such as greater than about 200 cP, such as greater than about 300 cP. The viscosity is generally less than about 1500 cP.

The injector can be designed to deliver a dose of fluid of greater than about 0.25 mL, such as greater than about 0.5 mL, such as greater than about 0.75 mL and generally less than about 5 mL, such as less than about 4 mL, such as less than about 3 mL. The injector can include a needle having a bore size of generally greater than about 0.08 mm, such as greater than about 0.1 mm, such as greater than about 0.12 mm, such as greater than about 0.14 mm, such as greater than about 0.16 mm, and generally less than about 0.3 mm, such as less than about 0.25 mm, such as less than about 0.22 mm, such as less than about 0.2 mm.

The injector can be designed to inject a fluid, such as a biologic, subcutaneously at a maximum force that is generally greater than about 2 N. The maximum force is the highest force before all contents are extruded from the injector. The maximum force can be greater than about 3 N, such as greater than about 4 N, such as greater than about 5 N, such as greater than about 6 N, such as greater than about 7 N, such as greater than about 8 N, such as greater than about 10 N, such as greater than about 12 N. The maximum force is generally less than about 20 N. The pressure at which the fluid is emitted from the injector can generally be greater than about 100 mPa, such as greater than about 150 mPa, such as greater than about 175 mPa, such as greater than about 200 mPa, such as greater than about 225 mPa, such as greater than about 250 mPa, such certain about 275 mPa, such as greater than about 300 mPa, such as greater than about 325 mPa and generally less than about 1,000 mPa.

Properties

The polymer composition of the present disclosure can display excellent mechanical properties. For instance, the tensile modulus, determined according to ISO Test No. 527, of the composition or polymer article may be greater than about 7000 MPa, such as greater than about 7200 MPa, such as greater than about 7500 MPa, and generally less than about 15,000 MPa, such as less than about 10,000 MPa.

The break stress of the composition can generally be greater than about 100 MPa, such as greater than about 110 MPa, such as greater than about 115 MPa, such as greater than about 120 MPa and generally less than about 180 MPa. The break strain can generally be greater than about 2.0%, such as greater than about 2.3%, and generally less than about 4%. The composition can exhibit a Charpy notched impact strength when tested at 23° C. of greater than about 6 $kJ/m^2$, such as greater than about 8 $kJ/m^2$, such as greater than about 9 $kJ/m^2$ and generally less than about 20 $kJ/m^2$, such as less than about 15 $kJ/m^2$.

The polymer composition of the present disclosure, due to the presence of the one or more mold release agents, can display low part ejection forces when measured according to the "part ejection test." During the part ejection test, a molded part with specific dimensions is removed from a mold, such as after injection molding. A force transducer is then used to measure the amount of force needed to remove the part from the mold. Any suitable force transducer may be used as are well known in the art of injection molding. The force transducer can operate at a resolution of at least 0.21 ms/4800 Hz. The polymer composition of the present disclosure can display a part ejection force of less than about 700 N. The ejection force is generally greater than about 200 N. FIG. 3 illustrates the dimensions of the part that is molded according to the test. The part is molded using a shot weight of 39 grams.

The present disclosure may be better understood with reference to the following examples.

EXAMPLES

The following examples are given below by way of illustration and not by way of limitation. The following experiments were conducted in order to show some of the benefits and advantages of the present invention.

Example No. 1

Various polymer compositions containing glass fibers and a tribological modifier were formulated and tested for friction characteristics and physical properties. Each of the compositions contained a polybutylene terephthalate polymer, a polyethylene terephthalate polymer, and glass fibers in an amount of 22% by weight. An ultra-high molecular weight silicone was then added to the composition with a polyester elastomer. Each composition contained a talc nucleant.

Four different compositions were formulated. The first composition contained no mold release agents. The second composition contained a non-polar mold release agent, the third composition contained a polar mold release agent, and the fourth composition contained a combination of a non-polar mold release agent and a polar mold release agent.

The following compositions were formulated and tested:

| Component | Sample No. 1 | Sample No. 2 | Sample No. 3 | Sample No. 4 |
|---|---|---|---|---|
| Polyethylene terephthalate | 12.5 | 12.5 | 12.5 | 12.5 |
| Polybutylene terephthalate | 59.35 | 59.1 | 59.1 | 59.1 |
| Glass fiber | 22.0 | 22.0 | 22.0 | 22.0 |
| Talc nucleant | 0.15 | 0.15 | 0.15 | 0.15 |
| Ultrahigh molecular weight polysiloxane and polyester elastomer (1:1 ratio) | 6.0 | 6.0 | 6.0 | 6.0 |
| Non-polar polyethylene wax | — | 0.25 | — | 0.125 |
| Polar oxidized polyethylene wax | — | — | 0.25 | 0.125 |

The components of each respective composition were mixed together and compounded using a ZSK 25MC (Werner & Pfleiderer, Germany) twin screw extruder. The screw configuration with kneading elements was chosen so that effective thorough mixing of the components took place. The compositions were extruded and pelletized. The pellets were dried for 4 hours at 120° C. and then injection molded.

The compositions/molds were tested for a variety of tribological and physical properties.

Stick-slip tests were conducted to determine the dynamic coefficient of friction. Stick-slip tests were conducted according to VDA 230-206. A ball-on-plate configuration was utilized with a load of 30 N, a sliding speed of 8 mm/s, and a test duration of 1000 cycles.

The compositions formulated according to the present disclosure were formed into plates for the dynamic coefficient of friction test. In a first set of experiments, the compositions were tested against a ball made from polycarbonate and acrylonitrile butadiene styrene polymer blend (CYCOLOY 01204H from Sabic). The following results were obtained:

| No. | Dynamic CoF | Wear track width (mm) | Static CoF |
|---|---|---|---|
| 1 | 0.046 | 0.04 | 0.06 |
| 2 | 0.046 | 0.04 | 0.059 |
| 3 | 0.048 | 0.02 | 0.059 |
| 4 | 0.047 | 0.00 | 0.062 |

The compositions were also tested for physical properties. Tensile properties were tested according to ISO Test 527:2012. Notched Charpy impact strength was tested according to ISO Test 179-1:2010. The test was run using a Type A notch (0.25 mm base radius) and Type 1 specimen size (length of 80 mm, width of 10 mm, and thickness of 4 mm). The test was conducted at a temperature of 23° C. The following results were obtained:

| Property | Sample No. 1 | Sample No. 2 | Sample No. 3 | Sample No. 4 |
|---|---|---|---|---|
| Tensile modulus (MPa) | 7790 | 7840 | 7760 | 7810 |
| Break stress (MPa) | 123 | 119 | 123.5 | 121.5 |
| Break strain (%) | 2.6 | 2.4 | 2.7 | 2.5 |
| Charpy notched @ 23° C. (kJ/m$^2$) | 10.5 | 10 | 10.5 | 10.5 |

The different polymer compositions were also tested for part ejection force according to the part ejection test described above. Sample No. 1 displayed a part ejection force of 714 N. Sample No. 2 displayed a part ejection force of 852 N. Sample No. 3 displayed a part ejection force of 1,087 N. Sample No. 4 displayed a part ejection force of 679 N. The different formulations were also subjected to a mold deposit study. Mold deposits were observed after 5,000 molding shots. A disk was molded during each shot. The amount of mold deposits was observed and ranked according to a ranking system of 1, 2 or 3 where 3 represents the most mold deposits and a ranking of 1 indicates no or only traces of scratchable material inside the mold. Sample No. 1 displayed a ranking of 3, Sample No. 2 displayed a ranking of 2, while Sample Nos. 3 and 4 displayed a ranking of only 1.

Sample No. 4 above was further tested for creep performance and stability after exposure to gamma rays.

Creep was measured at 20 MPa, 40 MPa, and 60 MPa for 1000 hours at 23 degrees C. The following results were obtained:

| CREEP MODULUS ISO Test 899-1 | UNITS | Sample No. 4 |
|---|---|---|
| 1000 hrs, 20 MPa | MPa | 5972 |
| 1000 hrs, 40 MPa | MPa | 4861 |
| 1000 hrs, 60 MPa | MPa | 4164 |

As shown, the composition displayed a creep modulus of greater than about 5000 MPa, such as greater than about 5200 MPa, such as greater than about 5400 MPa, such as greater than about 5600 MPa, such as greater than about 5800 MPa, and less than about 7000 MPa when tested at 20 MPa. As shown, the composition displayed a creep modulus of greater than about 4300 MPa, such as greater than about 4400 MPa, such as greater than about 4500 MPa, such as greater than about 4600 MPa, such as greater than about 4700 MPa, and less than about 6500 MPa when tested at 40 MPa. When tested at 60 MPa, the composition displayed a creep modulus of greater than about 3500 MPa, such as greater than about 3700 MPa, such as greater than about 3900 MPa, such as greater than about 4000 MPa, such as greater than about 4100 MPa, and less than about 6000 MPa.

Test specimens made from Sample No. 4 were exposed to different levels of gamma radiation and then tested for tensile properties. The following results were obtained:

| Sample No. 4 | | |
|---|---|---|
| Gamma Dose [kGy] | Tensile Modulus [MPa] | Break Stress [MPa] |
| 0 | 7935 | 116.4 |
| 6 | 7802 | 117.3 |
| 12 | 7813 | 119.6 |
| 24 | 7804 | 118.7 |
| 48 | 7842 | 119.5 |

-continued

| Sample No. 4 | | |
|---|---|---|
| Gamma Dose [kGy] | Tensile Modulus [MPa] | Break Stress [MPa] |
| 96 | 7896 | 119.2 |
| 150 | 7856 | 118.5 |

As shown, the composition was extremely stable even after exposure to high levels of energy. As shown above, the tensile modulus decreased by less than about 5%, such as less than about 3%, such as less than about 2%, such as even less than about 1% after a 150 kGy gamma dose.

Example No. 2

Various different polymer compositions were formulated and tested for physical properties. The following compositions were formulated and tested.

| Component | Sample No. 5 | Sample No. 6 | Sample No. 7 | Sample No. 8 | Sample No. 9 | Sample No. 10 | Sample No. 11 |
|---|---|---|---|---|---|---|---|
| PBT (MVR 40 cm$^3$/10 min) | 99.60 | 99.40 | 99.40 | 99.40 | 99.40 | 99.40 | 99.40 |
| Talc nucleant | 0.15 | 0.20 | 0.20 | 0.20 | 0.20 | 0.20 | 0.20 |
| Calcium stearate | | 0.40 | | | | | |
| Montan wax. Ester of montanic acids with multifunctional alcohols. | 0.25 | | | | | | |
| Montan wax. Sodium soap of montanic acids | | | 0.40 | | | | |
| Amide wax. | | | | 0.40 | | | |
| Polyolefin wax, non-polar | | | | | 0.20 | | |
| Polyolefin wax/oxidized PE wax, polar (15-19 KOH/g) | | | | | 0.20 | 0.40 | |
| Rice bran wax/modified natural wax (45-55 KOH/g) | | | | | | | 0.40 |
| | 100.0 | 100.0 | 100.0 | 100.0 | 100.0 | 100.0 | 100.0 |

| Property | Condition | Sample No. 5 | Sample No. 6 | Sample No. 7 | Sample No. 8 | Sample No. 9 | Sample No. 10 | Sample No. 11 |
|---|---|---|---|---|---|---|---|---|
| Rheological Testing | Condition | | | | | | | |
| MVR | 250/2.16 | 40 | 42 | 39 | 41 | 41 | 41 | 40 |
| Mechanical Testing | Condition | | | | | | | |
| Tensile Strength at yield | 50 mm/min | 60 | 62 | 64 | 63 | 62 | 62 | 62 |
| Elongation at Yield | 50 mm/min | 4 | 10 | 10 | 10 | 10 | 10.5 | 10.5 |
| Tensile Strength at Break | 50 mm/min | 60 | 53 | 55 | 55 | 52 | 52 | 53 |
| Elongation at Break | 50 mm/min | 15 | 15 | 17 | 15 | 18 | 17 | 17 |
| Tensile Modulus | 1 mm/min | 2700 | 2700 | 2710 | 2700 | 2700 | 2715 | 2700 |

Sample Nos. 9 and 11 above show excellent physical properties in comparison to the other samples. In addition, these samples are formulated to produce polymer compositions with improved melt processing characteristics in order to reduce mold cycle times.

These and other modifications and variations to the present invention may be practiced by those of ordinary skill in the art, without departing from the spirit and scope of the present invention, which is more particularly set forth in the appended claims. In addition, it should be understood that aspects of the various embodiments may be interchanged both in whole or in part. Furthermore, those of ordinary skill in the art will appreciate that the foregoing description is by way of example only and is not intended to limit the invention so further described in such appended claims.

What is claimed:

1. A polymer composition comprising:
   a thermoplastic polymer;
   at least one of a tribological modifier or a nucleant;
   reinforcing fibers present in the polymer composition in an amount from 5% to about 55% by weight; and
   at least a first mold release agent and a second mold release agent, wherein the first mold release agent comprises a polar mold release agent comprising a polar wax, wherein the second mold release agent comprises a non-polar mold release agent comprising a non-polar polymer, and wherein the thermoplastic polymer is selected from a polyester polymer, a polyether ether ketone polymer, a polyphenylene sulfide polymer, or a polyacetal polymer.

2. A polymer composition as defined in claim 1, wherein each mold release agent is present in the polymer composition in an amount less than about 4% by weight and wherein the weight ratio between the polar mold release agent and the non-polar mold release agent is from about 10:1 to about 1:10.

3. A polymer composition as defined in claim 1, wherein the thermoplastic polymer comprises a polybutylene terephthalate polymer.

4. A polymer composition as defined in claim 1, wherein the polar mold release agent comprises a modified polyolefin.

5. A polymer composition as defined in claim 1, wherein the polar mold release agent comprises an oxidized polyethylene wax or a polyolefin polymer modified by maleic anhydride groups and wherein the non-polar polymer comprises a polyethylene wax.

6. A polymer composition as defined in claim 1, wherein the polar mold release agent has an acid value of from about 10 mg KOH/g to about 25 mg KOH/g.

7. A polymer composition as defined in claim 1, wherein the polar mold release agent has an acid value of from about 30 mg KOH/g to about 75 mg KOH/g.

8. A polymer composition as defined in claim 1, wherein the polar mold release agent comprises oxidized esters of fatty acids and wherein the oxidized esters of fatty acids are formed from at least 50% by weight of fatty acids having a carbon chain length of from about 20 carbon atoms to about 40 carbon atoms or wherein the oxidized esters of fatty acids are formed from at least 25% by weight of fatty acid having a carbon chain length of from about 40 carbon atoms to about 64 carbon atoms.

9. A polymer composition as defined in claim 2, wherein the polar wax and the non-polar polymer are each present in the polymer composition in an amount less than about 2% by weight and in an amount greater than 0.01% by weight.

10. A polymer composition as defined in claim 3, wherein the polymer composition contains the tribological modifier and wherein the tribological modifier comprises an ultra-high molecular weight silicone and is present in the polymer composition in an amount from about 0.1% to about 10% by weight.

11. A polymer composition as defined in claim 10, wherein the polybutylene terephthalate polymer is present in the composition in an amount from about 50% to about 90% by weight, the reinforcing fibers comprising glass fibers and being present in the polymer composition in an amount from 5% to about 30% by weight, and the ultra-high molecular weight silicone being present in the composition in an amount from about 0.5% to about 5% by weight.

12. A polymer composition as defined in claim 1, wherein every polymer component contained in the polymer composition complies with the United States Food and Drug Administration standards listed in 21 CFR 177.

13. A polymer composition as defined in claim 1, wherein the polymer composition further contains a mineral nucleant.

14. A polymer composition as defined in claim 13, wherein the mineral nucleant comprises talc, the talc being present in the polymer composition in an amount from about 0.01% by weight to about 1% by weight.

15. A polymer composition as defined in claim 1, wherein the polymer composition displays an adhesive force of less than about 700 N when tested according to the part ejection test.

16. A polymer composition as defined in claim 1, wherein the polymer composition exhibits a dynamic coefficient of friction according to VDA 230-206 of less than about 0.08 when tested against a polycarbonate and acrylonitrile butadiene styrene blend at a speed of 8 mm/s, at a load of 30 N and after 1,000 cycles.

17. A polymer composition as defined in claim 11, wherein the composition further contains a carrier polymer for the ultra-high molecular weight silicone, the carrier polymer comprising a polycarbonate polymer, a polyester elastomer, a polyethylene terephthalate polymer, and/or a copolyester.

18. A polymer composition as defined in claim 1, wherein the reinforcing fibers comprise glass fibers, the glass fibers being present in the polymer composition in an amount from about 5% to about 50% by weight.

19. A molded article made from the polymer composition as defined in claim 1.

20. A molded article as defined in claim 19, wherein the molded article comprises an injector, the injector for dispensing liquid medicaments, the injector including a needle that has a bore size of from about 0.08 mm to about 0.25 mm, the injector including a spring member that dispenses doses of a medicament at a maximum force of greater than about 3 N.

21. An apparatus comprising:
    a first sliding member in operative association with a second sliding member, the first sliding member and the second sliding member being configured to remain in contact and move relative to each other, and wherein the first sliding member and the second sliding member are both made from a polymer composition as defined in claim 1 and wherein the medical device comprises an inhaler, an injection device, a surgical instrument or a wearable device.

22. The polymer composition as defined in claim 1, wherein the wherein the polymer composition exhibits a wear track according to VDA 230-206 of 0.04 mm or less when tested against a polycarbonate and acrylonitrile butadiene styrene blend at a speed of 8 mm/s, at a load of 30 N and after 1,000 cycles.

23. An apparatus comprising:
a first sliding member in operative association with a second sliding member, the first sliding member and the second sliding member being configured to remain in contact and move relative to each other, and wherein the first sliding member and the second sliding member are both made from a polymer composition, wherein the medical device comprises an inhaler, an injection device, a surgical instrument or a wearable device, and wherein the polymer composition comprises a thermoplastic polymer, at least one of a tribological modifier or a nucleant, optionally reinforcing fibers present in the polymer composition in an amount from about 5% to about 55% by weight, and at least a first mold release agent and a second mold release agent, wherein the first mold release agent comprises a polar mold release agent comprising a polar wax, and wherein the second mold release agent comprises a non-polar mold release agent comprising a non-polar polymer.

24. A polymer composition comprising:
a thermoplastic polymer;
at least one of a tribological modifier or a nucleant;
optionally reinforcing fibers present in the polymer composition in an amount from about 5% to about 55% by weight; and
at least a first mold release agent and a second mold release agent, wherein the first mold release agent comprises a polar mold release agent comprising a polar wax, wherein the second mold release agent comprises a non-polar mold release agent comprising a non-polar polymer, and wherein every polymer component contained in the polymer composition complies with the United States Food and Drug Administration standards listed in 21 CFR 177.

* * * * *